United States Patent
Stack et al.

(10) Patent No.: US 7,381,723 B2
(45) Date of Patent: Jun. 3, 2008

(54) AZABICYCLYLMETHYL DERIVATIVES OF 7,8-DIHYDRO-1,6,9,-TRIOXA-3-AZA-CYCLOPENTA[A]NAPHTHALENE AS 5-HT$_{1A}$ ANTAGONISTS

(75) Inventors: Gary P. Stack, Ambler, PA (US);
Megan Tran, Hoboken, NJ (US);
Adam M. Gilbert, Congers, NY (US)

(73) Assignee: Wyeth, Madison, NJ (US)

( * ) Notice: Subject to any disclaimer, the term of this patent is extended or adjusted under 35 U.S.C. 154(b) by 338 days.

(21) Appl. No.: 10/878,715

(22) Filed: Jun. 28, 2004

(65) Prior Publication Data

US 2005/0085475 A1 Apr. 21, 2005

Related U.S. Application Data

(63) Continuation of application No. 10/131,917, filed on Apr. 25, 2002, now Pat. No. 6,780,860.

(60) Provisional application No. 60/286,818, filed on Apr. 26, 2001.

(51) Int. Cl.
| | |
|---|---|
| A01N 43/66 | (2006.01) |
| A01N 43/54 | (2006.01) |
| A01N 43/42 | (2006.01) |
| A61K 31/53 | (2006.01) |
| A61K 31/44 | (2006.01) |
| C07D 239/42 | (2006.01) |
| C07D 401/04 | (2006.01) |
| C07D 403/00 | (2006.01) |
| C07D 401/00 | (2006.01) |
| C07D 405/00 | (2006.01) |
| C07D 411/00 | (2006.01) |
| C07D 413/00 | (2006.01) |
| C07D 417/00 | (2006.01) |
| C07D 419/00 | (2006.01) |
| C07D 421/00 | (2006.01) |
| C07C 409/00 | (2006.01) |

(52) U.S. Cl. ............... 514/241; 514/256; 514/304; 544/209; 544/333; 546/126

(58) Field of Classification Search ............... None
See application file for complete search history.

(56) References Cited

U.S. PATENT DOCUMENTS 5,318,988 A  6/1994 Schohe-Loop et al. ..... 514/458

5,371,094 A  12/1994  Heine et al. ............ 514/323

FOREIGN PATENT DOCUMENTS

| EP | 1 083 178 | 3/2001 |
|---|---|---|
| JP | 11180979 | 6/1999 |
| WO | WO 91/13872 A1 | 9/1991 |
| WO | WO 97/23485 A1 | 7/1997 |
| WO | WO 98/40386 A1 | 9/1998 |

OTHER PUBLICATIONS

Robichaud, A.J. et al., Ann. Reports Med. Chem., 38, 2000, 11-20.*
Gaster, L.M. et. al., Ann. Reports of Med. Chem., 33, 1998, 21-30.*
Logan, R.H., Ammonolysis of Acyl Halide to Amides; p. 3-4.*
M. Carli et al., Neuropharmacology, 1999, 38(8), 1165-1173.
Carl Boast et al., Neurobiology of Learning and Memory, 1999, 7(13), 259-271.
Alfredo Meneses et al., Neurobiology of Learning and Memory, 1999, 71(2), 207-218.
Michael D. Ennis et al., J. Med. Chem., 1992, 35, 3058-3066.
Robichaud, A.J. et al., Ann. Reports Med. Chem., 2000, 38, 11-20.
Gaster, L.M. et al., Ann. Reports Med. Chem., 1998, 33, 21-30.

* cited by examiner

Primary Examiner—James O. Wilson
Assistant Examiner—Jeffrey H Murray
(74) Attorney, Agent, or Firm—Woodcock Washburn LLP

(57) ABSTRACT

Compounds of the formula

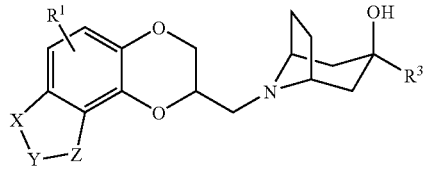

are useful for treating the cognitive deficits due to aging, stroke, head trauma, Alzheimer's disease or other neurodegenerative diseases, or schizophrenia and are also useful for the treatment of disorders such as anxiety, aggression and stress, and for the control of various physiological phenomena, such eating disorders, disorders of thermoregulation, and sleep and sexual dysfunction.

20 Claims, No Drawings

AZABICYCLYLMETHYL DERIVATIVES OF 7,8-DIHYDRO-1,6,9,-TRIOXA-3-AZA-CYCLOPENTA[A]NAPHTHALENE AS 5-HT$_{1A}$ ANTAGONISTS

BACKGROUND OF THE INVENTION

This application is a continuation of U.S. application Ser. No. 10/131,917 filed Apr. 25, 2002, which claims priority from provisional application Ser. No. 60/286,818 filed on Apr. 26, 2001, each of which is hereby incorporated by reference in its entirety.

Recent studies with the selective 5-HT$_{1A}$ antagonist WAY-100635 have confirmed a role for 5-HT$_{1A}$ receptors in learning and memory. Carli et. al. (Neuropharmacology (1999), 38(8), 1165-1173) demonstrated that WAY-100635 prevented the impairment of spatial learning caused by intrahippocampal injection of 3-[(R)-2-carboxypiperazin-4-yl]propyl-1-phosphonic acid (CPP), a competitive NMDA receptor antagonist, in a two-platform spatial discrimination task. Boast et. al. (Neurobiol. Learn. Mem. (1999), 71(3) 259-271) found that WAY-100635 significantly reduced the cognitive impairment induced by the non-competitive NMDA antagonist MK801, as determined by the performance of rats trained on a delayed nonmatching to sample radial arm maze task. Menesis et. al. (Neurobiol. Learn. Mem. (1999), 71(2) 207-218) showed that post-training administration of WAY-100635 reversed the learning deficit induced by scopolamine, a cholinergic antagonist, in an autoshaping learning task. New and novel 5-HT$_{1A}$ antagonists would be useful for these and other uses.

DESCRIPTION OF THE INVENTION

In accordance with this invention, there is provided a group of novel 5-HT$_{1A}$ antagonists of the formula I:

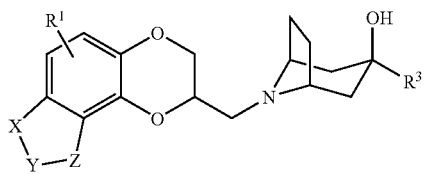

wherein

R$^1$ is hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

X—Y-Z is N=C(R$^2$)—O, N=C(R$^2$)—NH or NH—C(R$^2$)=CH;

R$^2$ is hydrogen, halo, trifluoromethyl, amino, mono- or di-alkylamino in which each alkyl group has 1 to 6 carbon atoms, alkoxy of one to six carbon atoms or alkyl of one to six carbon atoms; and R$^3$ is phenyl, naphthyl, anthracyl, phenanthryl, pyridyl, pyrimidyl, triazinyl, thienyl, furyl, pyrrolyl, pyrazolyl, indolyl, imidazolyl, benzofuryl, benzothienyl, oxazolyl, or thiazolyl, each optionally substituted with from one to three substituents selected from hydroxy, halo, trifluoromethyl, cyano, amino, mono- or di-alkylamino in which each alkyl group has 1 to 6 carbon atoms, alkoxy of one to six carbon atoms and alkyl of one to six carbon atoms;

or a pharmaceutically acceptable salt thereof.

In some embodiments of the present invention X—Y-Z is N=C(R$^2$)—O.

R$^1$ is preferably hydrogen, halo, trifluoromethyl, alkyl of 1 to 6 carbon atoms, alkoxy of 1 to 6 carbon atoms, amino, mono- or di-alkylamino in which each alkyl group has 1 to 6 carbon atoms. In more preferred embodiments, R$^1$ is hydrogen, trifluoromethyl, alkyl of one to six carbon atoms or alkoxy of one to six carbon atoms.

In some embodiments of the present invention R$^2$ is preferably hydrogen, trifluoromethyl, amino, mono- or dialkylamino in which each alkyl group has one to six carbon atoms, or alkyl of 1 to 6 carbon atoms, R$^2$ is more preferably hydrogen, trifluoromethyl, or alkyl of one to six carbon atoms. R$^2$ is still more preferably hydrogen or alkyl of one to six carbon atoms and still more preferably alkyl from 1 to 3 carbon atoms.

In other embodiments of -the present invention R$^3$ is phenyl, naphthyl, pyridyl, pyrimidyl, thienyl, furyl, pyrrolyl, pyrazolyl, indolyl, imidazolyl, benzofuryl, or benzothienyl, each optionally substituted with from one to three substituents selected from hydroxy, halo, trifluoromethyl, cyano, amino, mono- or di-alkylamino in which each alkyl group has 1 to 6 carbon atoms, alkoxy of one to six carbon atoms and alkyl of one to six carbon atoms. R3 is more preferably phenyl, naphthyl, pyridyl, pyrrolyl, indolyl, or benzothienyl, each optionally substituted with from one to three substituents selected from halo, trifluoromethyl, cyano, alkoxy of one to six carbon atoms and alkyl of one to six carbon atoms R$^3$ is preferably phenyl or naphthyl, each optionally substituted with from one to three substituents selected from halo, trifluoromethyl, cyano, alkoxy of one to six carbon atoms and alkyl of one to six carbon atoms.

Still more preferred compounds are those in which R$^1$ is hydrogen, halo, trifluoromethyl, alkyl of one to six carbon atoms, alkoxy of one to six carbon atoms, amino, mono- or di-alkylamino in which each alkyl group has one to six carbon atoms; R$^2$ is hydrogen, trifluoromethyl, amino, mono- or di-alkylamino in which each alkyl group has one to six carbon atoms, or alkyl of one to six carbon atom; and R$^3$ is phenyl, naphthyl, pyridyl, pyrimidyl, thienyl, furyl, pyrrolyl, pyrazolyl, indolyl, imidazolyl, benzofuryl, or benzothienyl, each optionally substituted with from one to three substituents selected from hydroxy, halo, trifluoromethyl, cyano, amino, mono- or di-alkylamino in which each alkyl group has 1 to 6 carbon atoms, alkoxy of one to six carbon atoms and alkyl of one to six carbon atoms.

Most preferred are those in which R$^1$ is hydrogen, halo, trifluoromethyl, alkyl of one to six carbon atoms or alkoxy of one to six carbon atoms; R$^2$ is hydrogen, trifluoromethyl or alkyl of one to six carbon atom; and R$^3$ is phenyl, naphthyl, pyridyl, pyrrolyl, indolyl, or benzothienyl, each optionally substituted with from one to three substituents selected from halo, trifluoromethyl, cyano, alkoxy of one to six carbon atoms and alkyl of one to six carbon atoms.

This invention relates to both the R and S stereoisomers of the 8-aminomethyl-7,8-dihydro-1,6,9-trioxa-3-aza-cyclopenta[a]naphthalene, as well as to mixtures of the R and S stereoisomers. Throughout this application, the name of the product of this invention, where the absolute configuration of the 8-aminomethyl-7,8-dihydro-1,6,9-trioxa-3-aza-cyclopenta[a]naphthalene is not indicated, is intended to embrace the individual R and S enantiomers as well as mixtures of the two. In some preferred embodiments of the present invention the S isomer is preferred.

Where a stereoisomer is preferred, it may, in some embodiments be provided substantially free of the corresponding enantiomer. Thus, an enantiomer substantially free of the corresponding enantiomer refers to a compound which is isolated or separated via separation techniques or prepared free of the corresponding enantiomer. Substantially free, as used herein means that the compound is made up of a significantly greater proportion of one stereoisomer. In preferred embodiments the compound is made up of at least about 90% by weight of a preferred stereoisomer. In other embodiments of the invention, the compound is made up of at least about 99% by weight of a preferred stereoisomer. Preferred stereoisomers may be isolated from racemic mixtures by any method known to those skilled in the art, including high performance liquid chromatography (HPLC) and the formation and crystallization of chiral salts or by methods described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

Alkyl as used herein refers to an aliphatic hydrocarbon chain and includes straight and branched chains such as methyl, ethyl, n-propyl, isopropyl, n-butyl, isobutyl, sec-butyl, t-butyl, n-pentyl, isopentyl, neo-pentyl, n-hexyl, and isohexyl. Lower alkyl refers to alkyl having 1 to 3 carbon atoms.

Alkanamido as used herein refers to the group R—C(=O)—NH— where R is an alkyl group of 1 to 5 carbon atoms.

Alkanoyloxy as used herein refers to the group R—C(=O)—O— where R is an alkyl group of 1 to 5 carbon atoms.

Alkanesulfonamido as used herein refers to the group R—S(O)$_2$—NH— where R is an alkyl group of 1 to 6 carbon atoms.

Alkoxy as used herein refers to the group R—O— where R is an alkyl group of 1 to 6 carbon atoms.

Carboxamido, as used herein refers to the group —CO—NH$_2$.

Carboalkoxy as used herein refers to the group R—O—C(=O)— where R is an alkyl group of 1 to 5 carbon atoms.

Halogen (or halo) as used herein refers to chlorine, bromine, fluorine and iodine.

Pharmaceutically acceptable salts are those derived from such organic and inorganic acids as: acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

Specific compounds of Formula I include:
8-{[2-Methyl-7,8-dihydro[1,4]dioxino[2,3-g][1,3]benzoxazol-8-yl]methyl}-3-phenyl-8-azabicyclo[3.2.1]octan-3-ol;
8-([2-Methyl-7,8-dihydro[1,4]dioxino[2,3-g][1,3]benzoxazol-8-yl]methyl}-3-[3-(trifluoromethyl)phenyl]-8-azabicyclo[3.2.1]octan-3-ol;
8-{[2-Methyl-7,8-dihydro[1,4]dioxino[2,3-g][1,3]benzoxazol-8-yl]methyl}-3-(2-naphthyl)-8-azabicyclo[3.2.1]octan-3-ol.

Compounds of the present invention are prepared in accordance with the following schemes and specific examples. Variables used are as defined for Formula I unless otherwise noted.

The 8-azabicyclylmethyl-7,8-dihydro-1,6,9-trioxa-3-azacyclopenta-[a]-naphthalenes of the invention are prepared as illustrated in Scheme I, below. Specifically, the appropriately substituted nitroguaiacol is alkylated with allyl bromide in the presence of a suitable base such as sodium hydride and then demethylated by a reagent such as sodium hydroxide. The resulting 4-nitro-2-allyloxyphenol is then alkylated with glycidyl tosylate or an epihalohydrin in the presence of a base such as sodium hydride and heated in a high boiling solvent such as mesitylene or xylene to effect both rearrangement of the allyl group and cyclization of the dioxan ring. The resulting primary alcohol is converted to the tosylate by reaction with p-toluenesulfonyl chloride in the presence of a tertiary amine or pyridine or alternatively to a halide by reaction with carbon tetrabromide or carbon tetrachloride in combination with triphenylphosphine. The allyl side chain is then isomerized by treatment with catalytic bis-acetonitrile

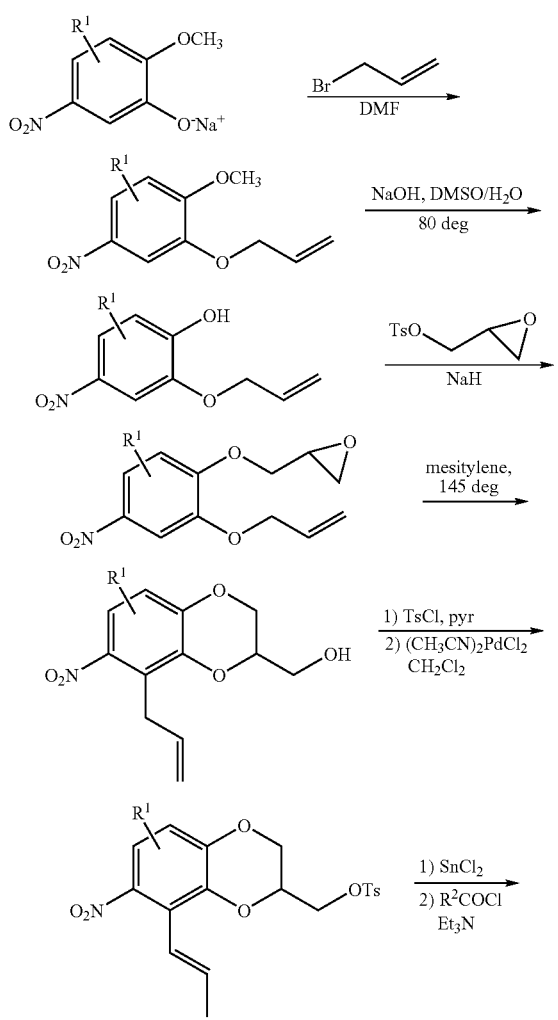

Scheme I

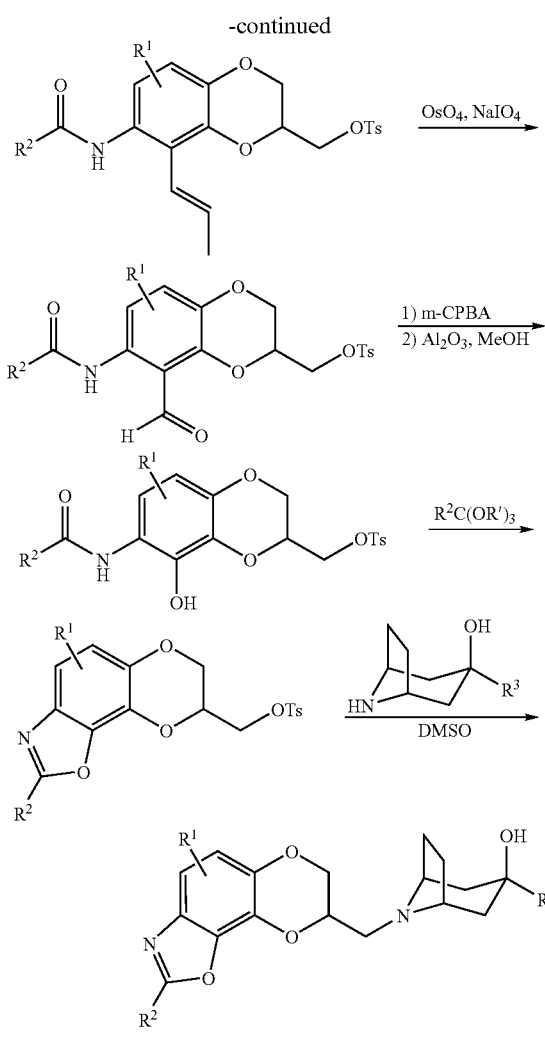

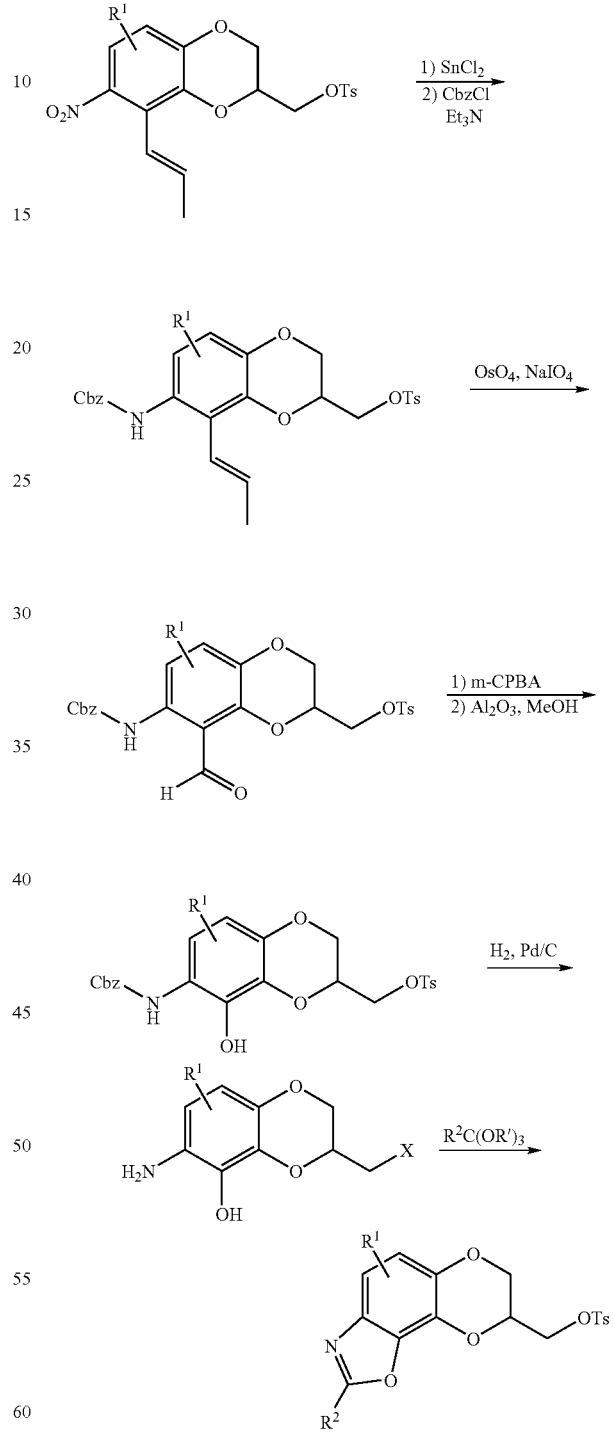

palladium (II) chloride in refluxing methylene chloride or benzene and the nitro group reduced to the aniline with a suitable reducing agent such as tin (II) chloride. The aniline is then acylated with the appropriate acyl halide or anhydride and the olefin cleaved to the corresponding o-amidobenzaldehyde by treatment with catalytic osmium tetroxide in the presence of sodium periodate. The aldehyde is converted to the phenol by treatment with meta-chloroperoxybenzoic acid in a Baeyer-Villager reaction and cyclization to the 7,8-dihydro-1,6,9-trioxa-3-aza-cyclopenta[a]naphthalene is effected by treatment at reflux with an appropriate dehydrating agent such as an ortho ester. Replacement of the tosylate or halide with the appropriately substituted azabicycle in some high boiling solvent such as dimethyl sulfoxide gives the title compounds of the invention.

Alternatively, as shown in Scheme II, the aniline produced by the tin (II) chloride reduction described above may be protected by a suitable protecting group such as carbobenzoxy (Cbz) before the olefin is cleaved to the aldehyde by treatment with osmium tetroxide/sodium periodate and the aldehyde converted to a phenol by the Baeyer-Villager procedure. Deprotection by treatment with hydrogen over palladium on carbon gives the o-aminophenol, which is cyclized to the 7,8-dihydro-1,6,9-trioxa-3-aza-cyclopenta[a] naphthalene by treatment with the appropriate ortho ester, carboxylic acid or anhydride. Treatment of the o-aminophenol with cyanogen bromide or chloride or a suitably substituted carbamoyl chloride leads to compounds of the invention in which $R^2$ is amino. Treatment of the o-aminophenol with carbonyl diimidazole gives the oxazolone which leads to compounds of the invention in which $R^2$ is halo via treatment with an inorganic anhydride such as phosphoryl chloride or bromide, or to compounds of the invention in which $R^2$ is alkoxy by treatment with the appropriate alkylating agent. Replacement of the tosylate with the appropriately substituted azabicycle as above gives the title compounds of the invention.

Compounds of the invention in which X—Y-Z is N=C($R^2$)—O, $R^1$ is hydrogen and $R^2$ is alkyl are most conveniently prepared according to scheme III below. The appropriate 2',3',4'-trihydroxyacylphenone is regioselectively alkylated with glycidyl tosylate or an epihalohydrin in the presence of a base such as sodium carbonate to give the corresponding 7-acyl-8-hydroxybenzodioxan-2-methanol. Following conversion of the ketone to the oxime by reaction with hydroxylamine hydrochloride and sodium acetate, cyclization to the oxazole is effected by treatment with phosphoryl chloride in the appropriate dimethylalkanoic acid amide. The resulting 7,8-dihydro-1,6,9-trioxa-3-azacyclopenta[a]naphthalene-8-methanol is converted to the tosylate by treatment with p-toluenesulfonyl chloride in pyridine and combined with the appropriate azabicycles as described to give the title compounds of the invention.

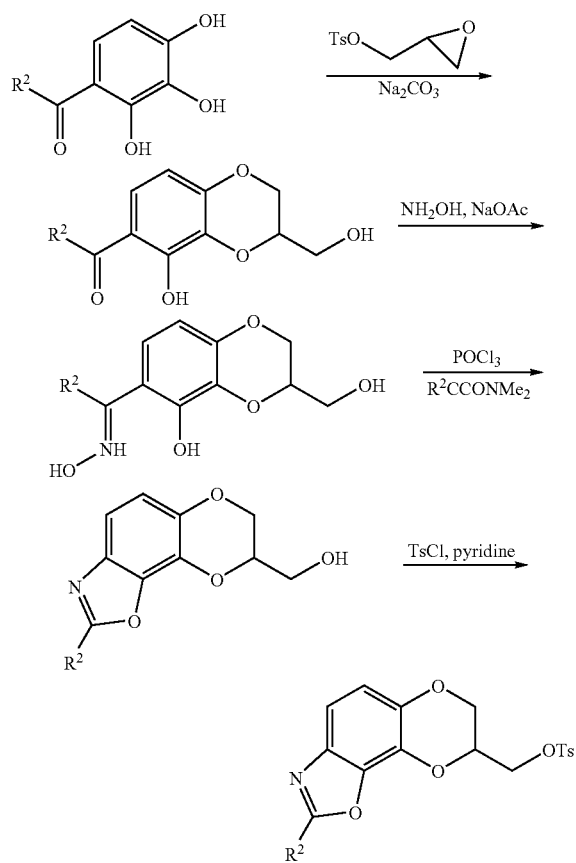

Scheme III 2,3-dihydro-7H-[1,4]dioxino[2,3-e]indoles of Formula I are prepared as described in Scheme IV. Specifically, the allyl side chain of the tosylate is cleaved to the aldehyde by treatment with ozone at low temperature, followed by work-up with a tertiary base such as diisopropylethylamine or triethylamine, or by treatment with catalytic osmium tetroxide and sodium periodate. Reduction of the nitro group with hydrogen over platinum oxide leads directly to formation of the indole in which $R^2$ is hydrogen. Alternatively, the aldehyde may be treated with an appropriate alkyl Grignard reagent or with trifluoromethyl trimethylsilane in the presence of cesium fluoride, then oxidized

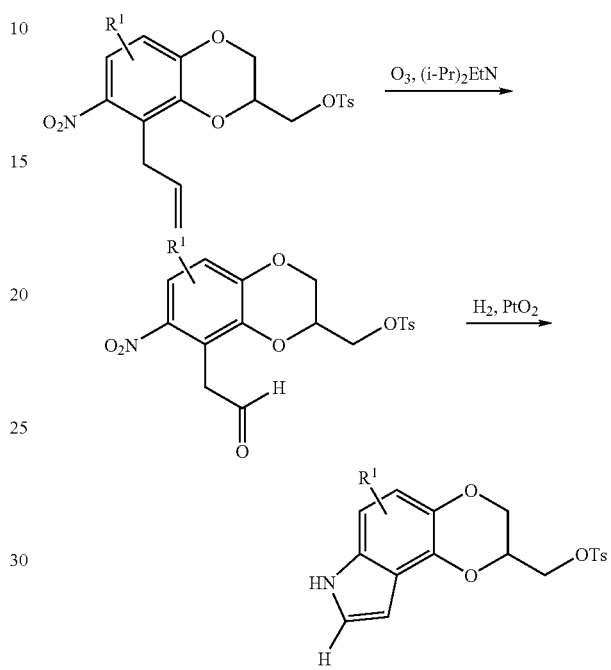

Scheme IV to a ketone with a suitable oxidant such as pyridinium chlorochromate (PCC) or the Swern reagent and reduced with hydrogen over platinum oxide to give the indoles in which $R^2$ is alkyl or trifluoromethyl. Replacement of the tosylate or halide with the appropriately substituted azabicycle in some high boiling solvent such as dimethyl sulfoxide gives the title compounds of the invention.

The compounds of the invention in which X—Y-Z is NH—C($R^2$)=CH and $R^2$ is a halogen such as chlorine or bromine are prepared from the nitroaldehyde described by the procedure of Scheme V. The aldehyde is oxidized to the phenylacetic acid by a suitable oxidant such as the Jones reagent ($CrO_3$, $H_2SO_4$ in acetone) and then the nitro group is reduced to the amine by treatment with hydrogen in the presence of a catalyst such as palladium on carbon. Cyclization to the oxindole is effected by treatment with acid and the oxindole converted to the

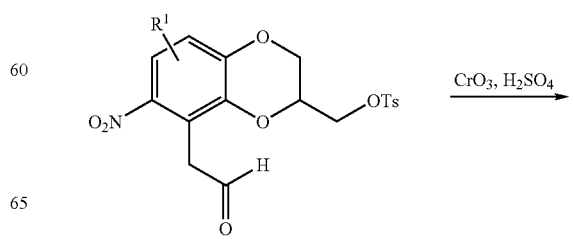

Scheme V

-continued

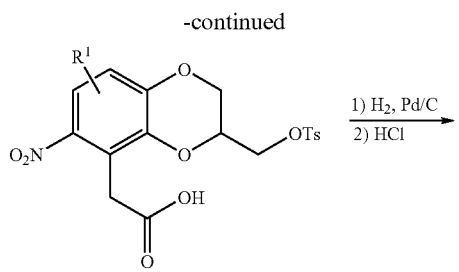

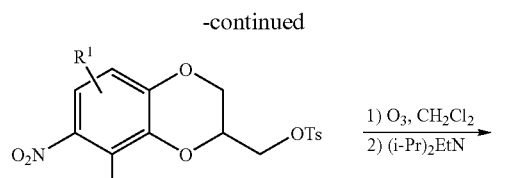

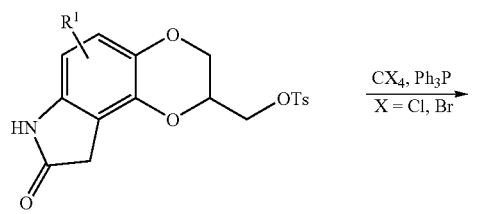

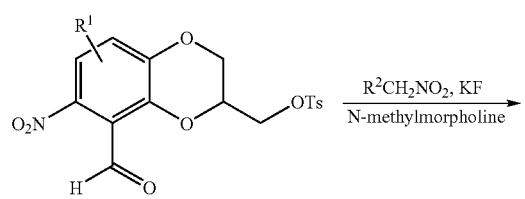

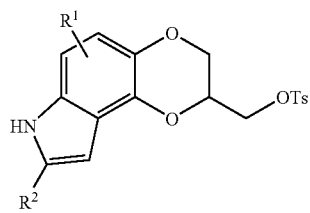

haloindole such as bromo or chloroindole via treatment with the appropriate carbon tetrahalide and triphenylphosphine in a solvent such as methylene chloride. Replacement of the tosylate with the appropriately substituted azabicycle in some high boiling solvent such as dimethyl sulfoxide gives the title compounds of the invention.

Such compounds of the invention may alternatively be prepared from the 7-nitro-8-allyl benzodioxan derived from the Claisen rearrangement by the procedure of Scheme VI. The alcohol is converted to the tosylate or halide as described above and the double bond is isomerized by treatment with bis-acetonitrile palladium (II) chloride in refluxing methylene chloride or benzene. Cleavage of the olefin with ozone or osmium tetroxide/periodate gives the o-nitrobenzaldehyde, which is condensed with the appropriate nitroalkane in the presence of a suitable base catalyst to yield the corresponding α,β-dinitrostyrene. Reduction of both nitro groups with hydrogen over palladium on carbon is accompanied by cyclization to form the indole. Replacement of the tosylate with the appropriately substituted azbicycle as above, gives the title compounds of the invention.

Scheme VI

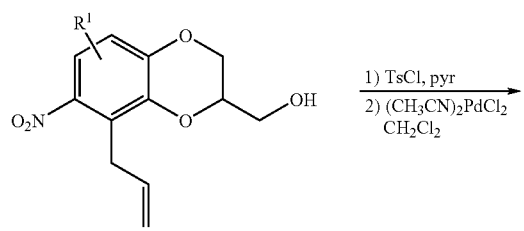

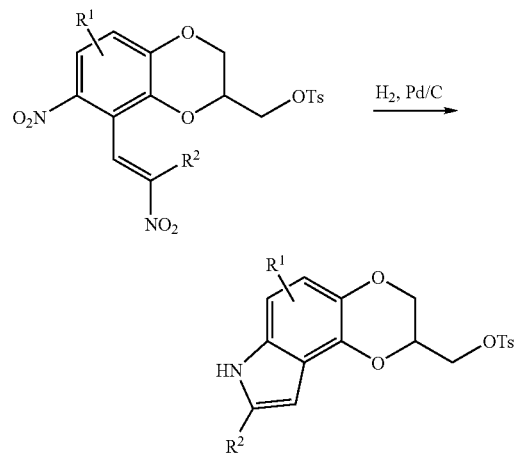

Compounds of the invention in which X—Y-Z is NH—C($R^2$)=CH and $R^2$ is methyl may be most conveniently prepared from the 7-nitro-8-allyl benzodioxan (6) described above by the procedure of Scheme VII. The nitro group is Scheme VII

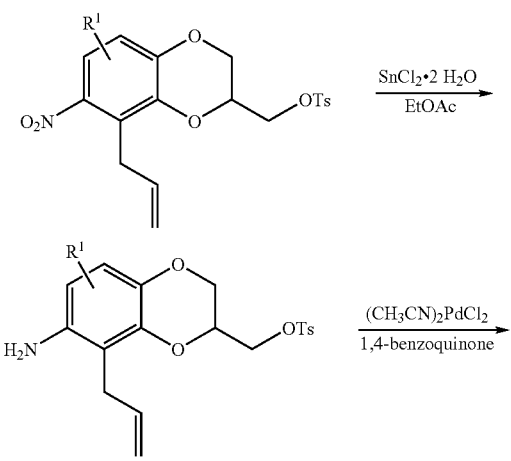

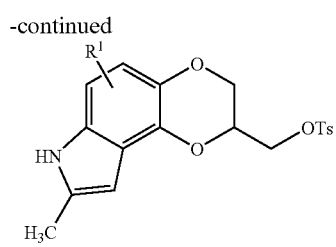

reduced with tin (II) chloride dihydrate in refluxing ethyl acetate to produce and cyclization to the 2-methylindole effected by several days' treatment with catalytic bis-acetonitrile (II) chloride, lithium chloride and 1,4-benzoquinone at room temperature in tetrahydrofuran. Replacement of the tosylate with the appropriately substituted azabicycle as above gives the title compounds of the invention Compounds of the invention where X—Y-Z is N=C(R$^2$)—NH are prepared as illustrated in Scheme VIII below. Specifically, the allyl side chain is isomerized by treatment with catalytic bis-acetonitrile palladium (II) chloride in refluxing methylene chloride or benzene and cleaved to the corresponding o-nitrobenzaldehyde by treatment with ozone followed by diisopropylethylamine or by catalytic osmium tetroxide in the presence of sodium periodate. The aldehyde is oxidized to the o-nitrobenzoic acid by a suitable oxidant such as chromium trioxide (Jones' oxidation) or sodium chlorite and the acid converted to the o-nitroaniline with diphenylphosphoryl azide (DPPA) in the presence of a tertiary base such as diisopropylethylamine (Curtius reaction). Reduction of the resulting nitroaniline to the diamine is performed with hydrogen and palladium on carbon and cyclization is achieved by treatment at reflux with the appropriate carboxylic acid. Refluxing the diamine dihydrochloride in higher boiling carboxylic acids occasionally causes replacement of a tosylate group with a chloride. Replacement of the tosylate or halide with the appropriately substituted azabicycle in some high boiling point solvent such as dimethylsulfoxide give the title compound of the invention.

Treatment of the diamine described in Scheme VIII, above, with cyanogen bromide or chloride or a suitably substituted carbamoyl chloride leads to compounds of the invention in which R$^2$ is amino. Treatment of the diamine with carbonyl diimidazole gives the imidazolone which leads to compounds of the invention in which X—Y-Z is N=C(R$^2$)—NH and R$^2$ is halo via treatment with an inorganic anhydride such as phosphoryl chloride or bromide, or to compounds of the invention in which N=C(R$^2$)—NH and R$^2$ is alkoxy by treatment with the appropriate alkylating agent. Replacement of the tosylate with the appropriately substituted azabicycle as above gives the title compounds of the invention.

Compounds of the invention in which N=C(R$^2$)—NH and R$^2$ is trifluoromethyl may also be conveniently prepared from the nitroaniline described above by the procedure illustrated below in Scheme IX. The nitroaniline is treated with trifluoroacetic anhydride in the presence of a suitable tertiary base such as diisopropylethylamine to yield the o-nitrophenyl trifluoroacetamide. This intermediate is reduced to the o-anilino trifluoroacetamide by treatment with hydrogen over palladium on carbon and cyclized to the trifluoromethylimidazole in refluxing trifluoroacetic acid. Replacement of the tosylate with the appropriately substituted azabicycle as above gives the title compounds of the invention.

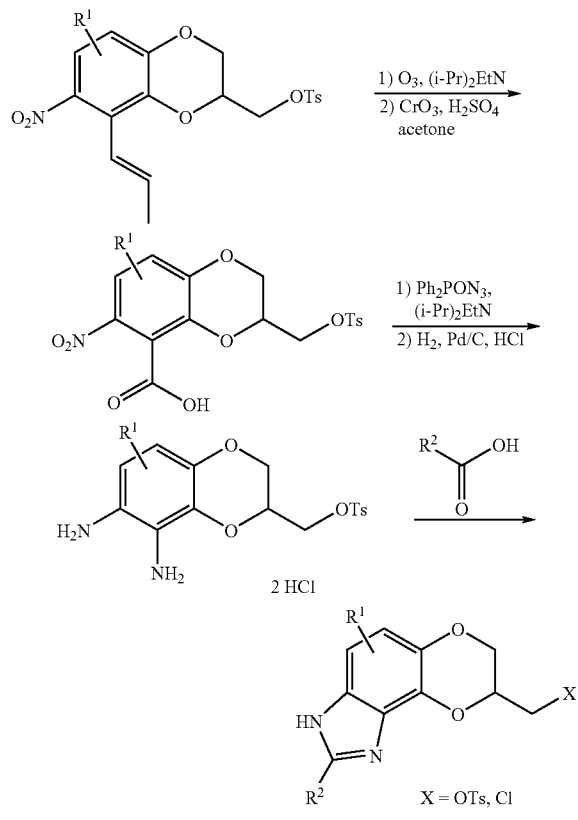

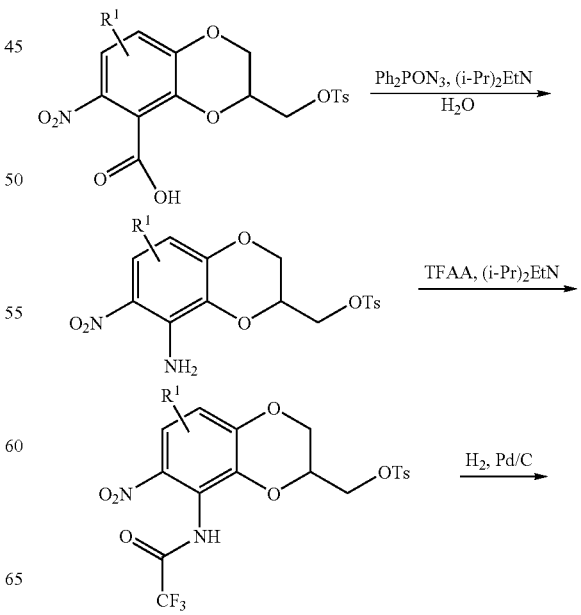

-continued

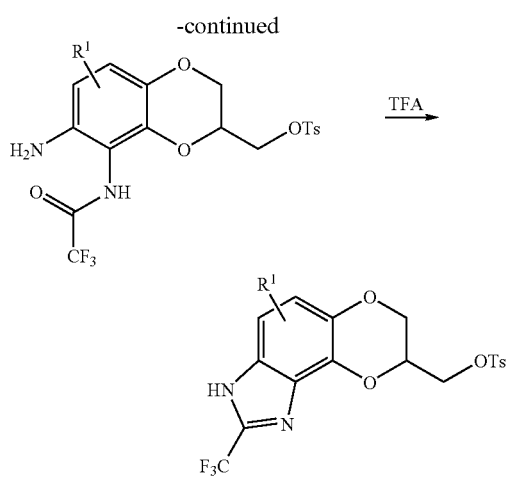

The azabicycles appropriate to the invention are known compounds or they may be prepared by the following procedure. Thus, tropinone is converted to the corresponding N-benzyltropinone by first reacting with 1-chloroethyl chloroformate in hot methylene chloride or 1,2-dichloroethane (DCE), treatment of the resulting carbamate with hot methanol, ethanol or similar alcohols and finally treatment with benzyl bromide, benzyl chloride or other benzylating agents known to the skilled artisan in a solvent such as tetrahydrofuran, benzene, N,N-dimethylformamide, or methylene chloride in the presence of a tertiary amine base. Benzyltropinone may be converted to the tropinol by reaction with an aryl lithium, aryl Grignard, or other aryl organometallics in a suitable solvent such as tetrahydrofuran or ether at −78° C., followed by warming to room temperature. The aryl organometallics used may be obtained from aryl halides as shown below. Aryl halides may be obtained commercially or by standard routes known to the skilled artisan. Only the product of exo addition is isolated as shown in the scheme below. The benzyl group may be removed via transfer hydrogenation over a precious metal catalyst such as palladium on carbon using formamide/methanol as the source of hydrogen.

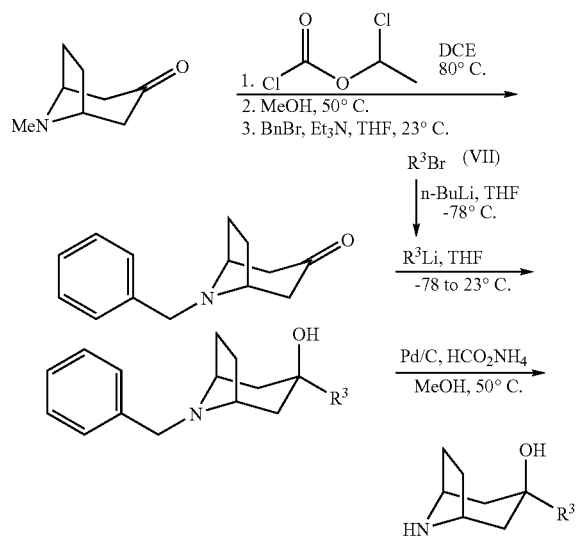

The guaiacols and 2',3',4'-trihydroxyacylphenones appropriate to the above chemistry are known compounds or can be prepared by one schooled in the art. The compounds of the invention may be resolved into their enantiomers by conventional methods or, preferably, the individual enantiomers may be prepared directly by substitution of (2R)-(−)-glycidyl 3-nitrobenzenesulfonate or tosylate (for the S benzodioxan methanamine) or (2S)-(+)-glycidyl 3-nitrobenzenesulfonate or tosylate (for the R enantiomer) in place of epihalohydrin or racemic glycidyl tosylate in the procedures above.

The 5-HT$_{1A}$ affinity of compounds of this invention was established in accordance with standard pharmaceutically accepted test procedures with representative compounds as follows.

High affinity for the serotonin 5-HT$_{1A}$ receptor was established by testing the claimed compound's ability to displace [$^3$H] 8-OH-DPAT (dipropylaminotetralin) from the 5-HT$_{1A}$ serotonin receptor following a modification of the procedure of Hall et al., J. Neurochem. 44, 1685 (1985) which utilizes CHO cells stably transfected with human 5-HT$_{1A}$ receptors. The 5-HT$_{1A}$ affinities for the compounds of the invention are reported below as K$_i$'s.

Antagonist activity at 5-HT$_{1A}$ receptors was established by using a $^{35}$S-GTPγS binding assay similar to that used by Lazareno and Birdsall (Br. J. Pharmacol. 109: 1120, 1993), in which the test compound's ability to affect the binding of $^{35}$S-GTPγS to membranes containing cloned human 5-HT$_{1A}$ receptors was determined. Agonists produce an increase in binding whereas antagonists produce no increase but rather reverse the effects of the standard agonist 8-OH-DPAT. The test compound's maximum inhibitory effect is represented as the I$_{max}$, while its potency is defined by the IC$_{50}$.

The results of the two standard experimental test procedures described in the preceding two paragraphs were as follows:

| Compound | 5-HT$_{1A}$ Receptor Affinity KI (nM) | 5-HT$_{1A}$ Function IC$_{50}$ (nM) (I$_{max}$) |
|---|---|---|
| Example 1 | 0.54 | 53.0 (76%) |
| Example 2 | 0.77 | — |
| Example 3 | 3.71 | 27.0 (95%) |

The compounds of this invention have potent affinity for and antagonist activity at brain 5-HT$_{1A}$ serotonin receptors. The compounds of the invention are thus exceedingly interesting for the treatment of cognitive dysfunction such as is associated with mild cognitive impairment (MCI) Alzheimer's disease and other dementias including Lewy Body, vascular, and post stroke dementias. Cognitive dysfunction associated with surgical procedures, traumatic brain injury or stroke may also be treated in accordance with the present invention. Further, compounds of the present invention may be useful for the treatment of diseases in which cognitive dysfunction is a co-morbidity such as, for example, Parkinson's disease, autism and attention deficit disorders.

Compounds of the present invention are also useful for treating cognitive deficits due to CNS disorders such as schizophrenia, (and other psychotic disorders such as paranoia and mano-depressive illness). The compounds are also useful for the treatment of disorders related to excessive serotonergic stimulation such as anxiety (e.g. generalized anxiety disorders, panic attacks, and obsessive compulsive disorders), aggression and stress. In addition, compounds of the present invention may be useful for the treatment of various physiological conditions such as Tourette's syndrome, migraine, autism, attention deficit disorders and hyperactivity disorders, sleep disorders, social phobias, pain, thermoregulatory disorders, endocrine disorders, urinary incontinence, vasospasm, stroke, eating disorders such as for example obesity, anorexia and bulimia, sexual dysfunction, and the treatment of alcohol, drug and nicotine withdrawal which are known to be, at least in part, under serotonergic influence. Finally, recent clinical trials employing drug mixtures (e.g. fluoxetine and pindolol) have demonstrated a more rapid onset of antidepressant efficacy for a treatment combining SSRI (serotonin selective reuptake inhibitor) activity and 5HT1A antagonism (Blier and Bergeron, 1995; F Artigas, et al., 1996, M. B. Tome et al., 1997). The compounds of the invention are thus interesting and useful as augmentation therapy in the treatment of depressive illness. Compounds of the present invention may thus be provided in combination with an antidepressant amount of a serotonin selective reuptake inhibitor to increase the onset of antidepressant efficacy. Such serotonin selective reuptake inhibitor includes, but is not limited to, fluoxetine, venlafaxine, citalopram, duloxetine, sertraline, paroxetine, fluvoxamine, nefazodone, and mirtazapine, and metabolites thereof.

Thus the present invention provides methods of treating, preventing, inhibiting or alleviating each of the maladies listed above in a mammal, preferably in a human, the methods comprising providing a pharmaceutically effective amount of a compound of this invention to the mammal in need thereof.

The present invention also provides methods of augmenting the treatment of depression by providing a mammal, preferably a human, with an antidepressant amount of a serotonin selective reuptake inhibitor (such as fluoxetine, venlafaxine, citalopram, duloxetine, sertraline, paroxetine, fluvoxamine, nefazodone, and mirtazapine, and metabolites thereof) and an amount of a compound of Formula I sufficient to hasten the onset of antidepressant efficacy.

Also encompassed by the present invention are pharmaceutical compositions for treating or controlling disease states or conditions of the central nervous system comprising at least one compound of Formula I, mixtures thereof, and or pharmaceutical salts thereof, and a pharmaceutically acceptable carrier therefore. Such compositions are prepared in accordance with acceptable pharmaceutical procedures, such as described in *Remingtons Pharmaceutical Sciences*, 17th edition, ed. Alfonoso R. Gennaro, Mack Publishing Company, Easton, Pa. (1985). Pharmaceutically acceptable carriers are those that are compatible with the other ingredients in the formulation and biologically acceptable. Pharmaceutical compositions of the present invention may further comprise a serotonin selective reuptake inhibitor such as, but not limited to fluoxetine, venlafaxine, citalopram, duloxetine, sertraline, paroxetine, fluvoxamine, nefazodone, and mirtazapine, and metabolites thereof.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The amount provided to a patient will vary depending upon what is being administered, the purpose of the administration, such as prophylaxis or therapy, and the state of the patient, the manner of administration, and the like. In therapeutic applications, compounds of the present invention are provided to a patient already suffering from a disease in an amount sufficient to cure or at least partially ameliorate the symptoms of the disease and its complications. An amount adequate to accomplish this is defined as a "therapeutically effective amount." The dosage to be used in the treatment of a specific case must be subjectively determined by the attending physician. The variables involved include the specific condition and the size, age and response pattern of the patient. Generally, a starting dose is about 5 mg per day with gradual increase in the daily dose to about 150 mg per day, to provide the desired dosage level in the human.

Provide as used herein means either directly administering a compound or composition of the present invention, or administering a prodrug, derivative or analog which will form an equivalent amount of the active compound or substance within the body.

The present invention includes prodrugs of compounds of Formula I. "Prodrug", as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). Design and Application of Prodrugs, Textbook of Drug Design and Development, Chapter 5, 113-191 (1991), Bundgaard, et al., Journal of Drug Deliver Reviews, 8:1-38(1992), Bundgaard, J. of Pharmaceutical Sciences, 77:285 et seq. (1988); and Higuchi and Stella (eds.) Prodrugs as Novel Drug Delivery Systems, American Chemical Society (1975).

The following examples illustrate the production of representative compounds of this invention.

INTERMEDIATE 1

3-Allyloxy-4-methoxynitrobenzene 97.5 g (0.51 mole) of the sodium salt of 5-nitroguaiacol was dissolved in one liter of DMF and 1.5 equivalents of allyl bromide added. The reaction was heated to 65° C. for two hours, after which time much of the dark color had discharged and tlc (1:1 $CH_2Cl_2$/hexane) indicated loss of starting material. The solvent was concentrated in vacuum and the residue washed with water. The product was isolated by filtration and dried in a vacuum. This gave 112 g of pale yellow solid. A sample recrystallized from methanol, gave m.p. 93-94° C.

INTERMEDIATE 2

2-Allyloxy-4-nitrophenol

To one liter of dimethyl sulfoxide was added 750 mL of 2 N aqueous sodium hydroxide and the mixture was heated to 65° C. The pale yellow solid 3-allyloxy-4-methoxynitrobenzene prepared above was added in portions over a 30 minute period and then the temperature was raised to 95° C. and maintained for 3 hours, after which time the starting material had been consumed. The mixture was allowed to cool and poured into a mixture of 1 L ice and 1 L 2 N HCl. 73 Grams of crude but homogeneous (by tlc 1:1 $CH_2Cl_2$/hexane) desired product was isolated as a light brown solid by filtration. This material was subsequently dissolved in 1:1 hexane/methylene chloride and filtered through silica gel to give 68 g of pale yellow solid, which, when recrystallized from ethyl/acetate/hexane, gave m.p. 61-62° C. The aqueous mother liquors from the initial crystallization above were extracted with 2 L of ethyl acetate. This was dried over sodium sulfate, filtered and evaporated to a dark oil. Column chromatography on silica with 1:1 $CH_2Cl_2$/hexane gave an additional 12 g of the title compound as a yellow solid. Elution with 2% MeOH in $CHCl_3$ gave 12 g of a dark oil which slowly crystallized in vacuum. This proved to be the Claisen product, 3-allyl4-nitrocatechol.

INTERMEDIATE 3

2-(2-Allyloxy-4-nitrophenoxymethyl)-oxirane 20 g (0.50 mole) of 60% NaH/mineral oil was placed in a two liter flask and washed with 500 mL of hexane. 1 L of DMF was added, followed by 77 g (0.40 mole) of the 2-allyloxy-4-nitrophenol prepared in the previous step. Addition of the phenol was performed in portions under argon. After stirring the mixture for 30 minutes at room temperature under argon, 108 g (0.48 moles) of (R)-glycidyl tosylate was added. and the mixture heated at 70-75° C. under nitrogen overnight. Upon cooling, the DMF was removed in vacuum and replaced with one liter of methylene chloride. This was washed with 500 mL portions of 2 N HCl, saturated sodium bicarbonate and saturated brine and dried over sodium sulfate. The mixture was filtered, concentrated to an oil in vacuum and column chromatographed on silica gel using 1:1 hexane/methylene chloride as eluant. This gave 43 g of product contaminated with traces of the two starting materials, followed by 21 g of pure product as a pale yellow solid. The impure material was recrystallized from 1.2 L of 10% ethyl acetate/hexane to give 34 g of pure (homogeneous on silica gel tlc with 1:1 hexane/methylene chloride) (R)-2-(2-allyloxy-4-nitrophenoxymethyl)-oxirane (m.p. 64° C.).

Elemental Analysis for: $C_{12}H_{13}NO_5$ Calc'd: C, 57.37; H, 5.21; N, 5.58 Found: C, 57.50; H, 5.21; N, 5.43

INTERMEDIATE 4

(8-Allyl-7-nitro-2,3-dihydro-benzo(1,4)dioxin-2-yl)-methanol (R)-2-(2-Allyloxy-4-nitrophenoxymethyl)-oxirane (20 g, 80 mmoles) prepared as above was heated at 155° C. in mesitylene for 24 hours under nitrogen. Filtration of the black solid which formed gave 1.5 g of very polar material. Evaporation of the solvent in vacuum followed by column chromatography on silica gel with methylene chloride as eluant gave 10 g of recovered starting material and 7.5 g of the desired rearranged (S)-(8-allyl-7-nitro-2,3-dihydro-benzo(1,4)dioxin-2-yl)-methanol, which slowly crystallized on standing in vacuum (m.p. 67° C.). The yield based on recovered starting material is 75%.

Elemental Analysis for: $C_{12}H_{13}NO_5$ Calc'd: C, 57.37; H, 5.21; N, 5.58 Found: C, 57.26; H, 5.20; N, 5.35

INTERMEDIATE 5

Toluene-4-sulfonic acid 8-allyl-7-nitro-2,3-dihydro-benzo(1,4)dioxin-2-ylmethyl ester 9.55 g (38.0 mmole) of (S)-(8-allyl-7-nitro-2,3-dihydro-benzo(1,4)dioxin-2-yl)-methanol was dissolved in 465 mL of pyridine, 29.0 g (152 mmole) of p-toluenesulfonyl chloride was added and the mixture stirred at room temperature under nitrogen overnight. Water was then added to quench the excess tosyl chloride and the solvent was removed in vacuum and replaced with methylene chloride. This solution was washed with 2 N HCl, with saturated sodium bicarbonate, and with saturated brine, and dried over magnesium sulfate. Filtration, evaporation in vacuum and column chromatography on silica gel with 1:1 hexane/methylene chloride as eluant gave 12.6 g (92%) of toluene-4-sulfonic acid (R)-allyl-7-nitro-2,3-benzo(1,4)dioxin-2-ylmethyl ester, which slowly crystallized to a tan solid (m.p. 60-62° C.) upon standing.

Elemental Analysis for: $C_{19}H_{19}NO_7S$ Calc'd: C, 56.29; H, 4.72; N, 3.45 Found: C, 56.13; H, 4.58; N, 3.44

INTERMEDIATE 6

{7-Nitro-8-[1-propenyl]-2,3-dihydro-1,4-benzo-dioxin-2-yl}methyl 4-methylbenzenesulfonate To a solution of 10.0 g (24.0 mmole) of (R)-[8-allyl-7-nitro-2,3-dihydro-1,4-benzodioxin-2-yl]methyl 4-methylbenzenesulfonate in 700 mL of benzene was added 1.03 g of bis(acetonitrile)dichloropalladium (II) and the mixture was refluxed under nitrogen for 48 hours. The catalyst was then removed by filtration and the filtrate concentrated in vacuum to a brown oil. Column chromatography on silica gel with methylene chloride as eluant gave 7.2 g of the title compound as a mixture of E and Z isomers. A sample of {(2R)-7-nitro-8[(E)-1-propenyl]-2,3-dihydro-1,4-benzo-dioxin-2-yl}methyl 4-methylbenzenesulfonate was obtained as a yellow solid (m.p. 105-106° C.) by evaporation of a pure E isomer-containing fraction.

Elemental Analysis for: $C_{19}H_{19}NO_7S$ Calc'd: C, 56.29; H, 4.72; N, 3.45 Found: C, 56.12; H, 4.64; N, 3.39

INTERMEDIATE 7

{7-Amino-8-[1-propenyl]-2,3-dihydro-1,4-benzo-dioxin-2-yl}methyl 4-methylbenzenesulfonate 10.0 g (24.0 mmole) of {(2R)-7-nitro-8-[1-propenyl]-2,3-dihydro-1,4-benzo-dioxin-2-yl}methyl 4-methylbenzenesulfonate and 28.0 g (123 mmole) of stannous chloride dihydrate were combined and heated to 70° C. in ethyl acetate (250 mL) for 6 hours under nitrogen. After cooling to room temperature, the reaction mixture was poured into ice and was made basic with sodium bicarbonate. It was then extracted with ethyl acetate, washed with brine, dried over magnesium sulfate, filtered and evaporated to a brown oil. The crude oil was then chromatographed on silica gel with 50% hexane/methylene chloride to remove impurities and the desired product was eluted with 0.5% methanol/$CH_2Cl_2$ to give 8.16 g (91%) of the (R)-enantiomer of the title compound as a yellow oil. For analytical purposes, 50 mg of the yellow oil was crystallized from ethanol with the addition of fumaric acid to give the fumarate of the title compound. MS (ESI) m/z 375 (M+H)+.

Elemental Analysis for: $C_{19}H_{21}NO_5S.1.00$ $C_4H_4O_4$ Calc'd: C, 56.20; H, 5.13; N, 2.85 Found: C, 56.40; H, 4.99; N, 2.91

INTERMEDIATE 8

{7{[(Benzyloxy)carbonyl]amino}-8-[1-propenyl]-2,3-dihydro-1,4-benzodioxin-2-yl}methyl 4-methyl-benzenesulfonate To a solution of {(2R)-7-amino-8-[1-propenyl]-2,3-dihydro-1,4-benzo-dioxin-2-yl}methyl 4-methylbenzenesulfonate (4.20 g, 11.2 mmole) in ethyl acetate (150 mL) was added benzyl chloroformate (8.00 mL, 56.0 mmole). The reaction mixture was stirred under nitrogen for 0.5 hour, then a solution of N,N-diisopropylethylamine (9.75 mL, 56 mmole) in ethyl acetate (75 mL) was added dropwise over a period of 0.5 hour. The mixture was stirred at room temperature under nitrogen overnight. The reaction was diluted in volume to 350 ml and was then washed with 2N HCl (2×100 mL), saturated sodium bicarbonate (150 mL) and brine (100 mL), dried over magnesium sulfate, filtered and evaporated to an oil. The crude oil was column chromatographed on silica gel with 10% ethyl acetate/hexane to remove impurities and the product eluted with 60% ethyl acetate/hexane to give the (R)-enantiomer of the title compound as a yellow oil (4.5 g, 79%). $^1H$ ($CDCl_3$) doublet 7.8 δ (2 ); multiplet 7.4 δ (7H); doublet 6.7 δ (2H); multiplet 6.0-6.2 δ (2H); singlet 5.2 δ (2H); multiplet 4.4 δ (1H); multiplet 4.2 δ (3H); multiplet 4.0 δ (1H); singlet 2.4 δ (3H); doublet 1.9 δ (3H).

INTERMEDIATE 9

{7{[(Benzyloxy)carbonyl]amino}-8-formyl-2,3-dihydro-1,4-benzodioxin-2-yl}methyl 4-methylbenzenesulfonate To a solution {(2R)-7-{[(benzyloxy)carbonyl]amino}-8-[1-propenyl]-2,3-dihydro-1,4-benzodioxin-2-yl}methyl 4-methylbenzenesulfonate (4.5 g, 8.84 mmole) in tetrahydrofuran (225 mL) was added $OsO_4$ (1.65 mL, 0.270 mmole). Then a solution of $NaIO_4$ (9.45 g, 44.2 mmole) in water (100 mL) was added dropwise. The reaction was stirred at room temperature under nitrogen overnight. Water (250 mL) was added to the mixture and it was then extracted with ethyl acetate. The organic phase was then washed with brine, dried over magnesium sulfate, filtered and evaporated to 4.45 g (>95%) of the (R)-enantiomer of the title compound as a yellow solid. $^1H$ ($CDCl_3$) broad singlet 10.8 δ (1H); singlet 10.1 δ (1H); doublet 7.9 δ (1H); doublet 7.8 δ (2H); multiplet 7.4 δ (7H); doublet 7.0 δ (1H); singlet 5.2 δ (2H); multiplet 4.5 δ (1H); multiplet 4.2 δ (3H); multiplet 4.1 δ (1H); singlet 2.4 δ (3H).

INTERMEDIATE 10

{7-{[(Benzyloxy)carbonyl]amino}-8-hydroxy-2,3-dihydro-1,4-benzodioxin-2-yl}methyl 4-methylbenzenesulfonate A solution of {(2R)-7-{[(benzyloxy)carbonyl]amino}-8-formyl-2,3-dihydro-1,4-benzodioxin-2-yl}methyl 4-methylbenzenesulfonate (4.45 g, 8.95 mmole) in methylene chloride (50 mL) was added dropwise to a solution of m-chloroperoxybenzoic acid (6.45 g, 22.4 mmole) in methylene chloride (120 mL). The reaction was stirred under nitrogen overnight. After dilution to 300 mL in volume, it was washed with saturated sodium bicarbonate (2×200 mL), brine (100 mL), dried over magnesium sulfate, filtered and evaporated to dryness. A $H^1$ NMR spectra was taken of the crude product and it was determined to be the formate ester. Cleavage was effected by stirring in methanol over basic alumina overnight. After filtration and evaporation, the product was purified by column chromatography on silica gel with hexane to remove the impurities, and the product eluted with methylene chloride to give the (R)-enantiomer of the title compound as a yellow oil (1.80 g, 40%). $^1H$ ($CDCl_3$) doublet 7.8 δ (2H); multiplet 7.2-7.4 δ (7H); broad singlet 7.0 δ (1H); doublet 6.4 δ (1H); singlet 5.2 δ (2H); multiplet 4.4 δ (1H); multiplet 4.2 δ (3H); multiplet 4.0 δ (1H); singlet 2.4 6 (3H).

INTERMEDIATE 11

{7-Amino-8-hydroxy-2,3dihydro-1,4-benzodioxin-2-yl}methyl 4-methylbenzenesulfonate A mixture of (2R)-7-{[(benzyloxy)carbonyl]amino}-8-hydroxy-2,3-dihydro-1,4-benzodioxin-2-yl}methyl 4-methylbenzenesulfonate (1.8 g, 3.7 mmole), 2.0 ml of 4.0 N isopropanolic HCl, and 0.25 q of 10% palladium on carbon in 200 mL of methanol was treated with 40 psi of hydrogen on a Parr shaker for 3 hours. The catalyst was filtered and washed with additional methanol. The solvent was evaporated in vacuum to yield 1.25 g (87%) of the (R)-enantiomer of the hydrochloride hemihydrate of the title compound as a beige foam.

Elemental Analysis for: $C_{16}H_{17}NO_6S \cdot 1.00\ HCl \cdot 0.5\ H_2O$ Calc'd: C, 48.43; H, 4.83; N, 3.53 Found: C, 48.21; H, 4.34; N, 3.58

INTERMEDIATE 12

7.8-Dihydro[1,4]dioxino[2,3-g][1,3]benzoxazol-8-ylmethyl 4-methylbenzenesulfonate

[(2R)-7-Amino-8-hydroxy-2,3-dihydro-1,4-benzodioxin-2-yl]methyl 4-methyl-benzenesulfonate hydrochloride (1.05 g, 2.99 mmole) in trimethyl orthoformate (7 mL) was heated to reflux in the presence of 0.20 g of p-toluenesulfonic acid for 3 hours. The solvent was removed under high vacuum to yield a beige solid. The crude product was recrystallized from ethanol to give 0.81 g (75%) of the (R)-enantiomer of the title compound, MS (ESI) m/z 361 (M+H)+.

Elemental Analysis for: $C_{17}H_{15}NO_5S$ Calc'd: C, 56.50; H, 4.18; N, 3.88 Found: C, 56.10; H, 4.37; N, 3.69

INTERMEDIATE 13

1-[5-Hydroxy-3-(hydroxymethyl)-2,3-dihydro-1,4-benzodioxin-6-yl]-1-ethanone

To a solution of 2',3',4'-trihydroxyacetophenone (10.6 g, 63.0 mmole) in DMF (75 mL) was added potassium carbonate (17.4 g, 126 mmole). After 5 minutes (R)-glycidyl tosylate (9.67 g, 42.3 mmole) was added, then the heterogeneous mixture was heated to 70° C. for 3 hours. After removal of the solvent in vacuum, the residue was taken into water (800 mL) and was then extracted with ethyl acetate (4×300 mL). The combined organic layers were dried over magnesium sulfate, filtered and evaporate to dryness in vacuum. The crude brown oil thus obtained was column chromatographed on silica gel with 40% hexane/ethyl acetate as eluant to give the (S)-enantiomer of the title compound as a yellow oil which solidifies upon standing (7.5 g, 78%). MS (ESI) m/z 223 (M–H)–.

Elemental Analysis for: $C_{11}H_{12}O_5 \cdot 0.10\ H_2O$ Calc'd: C, 58.46; H, 5.44 Found: C, 58.02; H, 5.09

INTERMEDIATE 14

1-[5-Hydroxy-3-(hydroxymethyl)-2,3-dihydro-1,4-benzodioxin-6-yl]-1-ethanone oxime A solution of hydroxylamine hydrochloride (2.38 g, 34.2 mmole) in 1:1 ethanol/pyridine (100 mL) was added to a solution of 1-[(3S)-5-hydroxy-3-(hydroxymethyl)-2,3-dihydro-1,4-benzodioxin-6-yl]-1-ethanone (1.92 g, 8.57 mmole) in ethanol (200 mL). It was then heated to reflux under nitrogen for 5 hours. Upon cooling, the solvent was removed and replaced with ethyl acetate. The solution was then washed with water (200 mL) and with aqueous 2N HCl (100 mL), dried over magnesium sulfate, filtered and evaporated in vacuum to give 1.89 g (93%) of the (S)-enantiomer of the title compound as a gray solid, m.p. 162° C. MS (ESI) m/z 240 (M+H)+.

Elemental Analysis for: $C_{11}H_{13}NO_5 \cdot 0.35\ H_2O$ Calc'd: C, 53.81; H, 5.62; N, 5.71 Found: C, 53.51; H, 5.30; N, 5.58

INTERMEDIATE 15

[2-Methyl-7,8dihydro[1,4]dioxino[2,3-g][1,3]benzoxazol-8-yl]methanol 3.03 g (12.6 mmole) of 1-[(3S)-5-hydroxy-3-(hydroxymethyl)-2,3-dihydro-1,4-benzodioxin-6-yl]-1-ethanone oxime was dissolved in a mixture of 1:3 N,N-dimethylacetamide/acetonitrile (100 mL). The solution was cooled in an ice/water bath and a solution of phosphorus oxychloride (1.26 mL, 35 mmole) in 1:3 N,N-dimethylacetamide/acetonitrile (30 mL) was added. The reaction mixture was stirred under nitrogen over a period of 48 hours. It was then added to an ice cold, saturated solution of sodium acetate, extracted with ethyl acetate, dried over magnesium sulfate, filtered and evaporated in vacuum. The resulting crude oil was column chromatographed on silica gel with 60% hexane/ethyl acetate to remove impurities and the product eluted with 40% hexane/ethyl acetate. After evaporation of the solvent in vacuum, 2.08 g (75%) of the (S)-enantiomer of the title compound was obtained as a white solid, m.p. 120° C. MS (ESI) m/z 222 (M+H)+.

Elemental Analysis for: $C_{11}H_{11}NO_4 \cdot 0.20\ H_2O$ Calc'd: C, 58.77; H, 5.11; N, 6.23 Found: C, 58.93; H, 4.91; N, 6.14

INTERMEDIATE 16

[2-Methyl-7,8-dihydro[1,4]dioxino[2,3-g][1,3]benzoxazol-8-yl]methyl 4-methylbenzenesulfonate To a solution of [(8S)-2-methyl-7,8-dihydro[1,4]dioxino[2,3-g]-[1,3]benzoxazol-8-yl]methanol (1.80 g, 8.14 mmole) in methylene chloride (100 mL) was added p-toluenesulfonyl chloride (3.90 g, 20.4 mmole). The mixture was cooled in an ice bath and a solution of diisopropylethylamine (3.55 mL, 20.4 mmole) in methylene chloride (20 mL) was then added dropwise, followed by 4-dimethylaminopyridine (0.65 g, 5.30 mmole). The solution was allowed to warm to room temperature and was stirred under nitrogen overnight. The reaction was diluted to 500 mL in volume with methylene chloride, then washed with aqueous 2 N HCl (200 mL), with saturated aqueous sodium bicarbonate (200 mL), and with brine (150 mL), dried over magnesium sulfate, filtered and evaporated in vacuum to a yellow oil. The crude oil was column chromatographed on silica gel using methylene chloride to remove impurities and 3% methanol/methylene chloride to elute the (R)-enantiomer of the title compound, which becomes a white solid under vacuum (2.56 g, 84%), m.p. 123° C. MS (ESI) m/z 376 (M+H)+.

Elemental Analysis for: $C_{18}H_{17}NO_6S \cdot 0.20\ H_2O$ Calc'd: C, 57.04; H, 4.63; N, 3.70 Found: C, 56.75; H, 4.62; N, 3.51

EXAMPLE 1

8-{[2-Methyl-7,8-dihydro[1,4]dioxino[2,3-g][1,3]benzoxazol-8-yl]methyl}-3-phenyl-8-azabicyclo[3.2.1]octan-3-ol (8R)-2-Methyl-7,8-dihydro[1,4]dioxino[2,3-g][1,3]benzoxazol-8-ylmethyl 4-methylbenzenesulfonate (0.375 g, 1.00 mmole) and 3-phenyl-8-aza-bicyclo[3.2.1]-octan-3-ol (0.25 g, 1.2 mmole) were combined in 8 mL of DMSO. This solution was heated to 75-80° C. under nitrogen for 8 hours. After completion, the reaction was cooled to room temperature and diluted to 500 mL with ethyl acetate. The mixture was washed twice with 400 mL portions of saturated aqueous sodium bicarbonate, with 300 mL of water and twice with 400 mL of saturated brine, dried over sodium sulfate, filtered and concentrated in vacuum. The crude oil was column chromatographed on silica gel using first methylene chloride to remove impurities and then 0.5% methanol/ methylene chloride to give, after concentration of the product fractions in vacuum, 0.12 g of the (S)-enantiomer of the title compound as an off-white solid, m.p. 203-205° C.

Elemental Analysis for: $C_{24}H_{26}N_2O_4 \cdot 0.10\ CH_2Cl_2$ Calc'd: C, 69.76; H, 6.36; N, 6.75 Found: C, 69.83; H, 6.52; N, 6.77

EXAMPLE 2

8-{[2-Methyl-7,8-dihydro[1,4]dioxino[2,3-g][1,3] benzoxazol-8-yl]methyl}-3-[3-(trifluoromethyl)phenyl]-8-azabicyclo[3.2.1]octan-3-ol (8R)-2-Methyl-7,8-dihydro[1,4]dioxino[2,3-g][1,3]benzoxazol-8-ylmethyl 4-methylbenzenesulfonate (0.40 g, 1.1 mmole) and 3-(3-trifluoromethyl-phenyl)-8-aza-bicyclo[3.2.1]octan-3-ol (0.50 g, 1.8 mmole) were combined in 8 mL of DMSO. This solution was heated at 82° C. under nitrogen for 6 hours. After completion, the reaction was cooled to room temperature and diluted to 500 mL with ethyl acetate. The mixture was washed twice with 400 mL portions of saturated aqueous sodium bicarbonate, with 300 mL of water and twice with 400 mL of saturated brine, dried over sodium sulfate, filtered and concentrated in vacuum to give 0.52 g of a brown oil. The crude oil was column chromatographed on silica gel using first methylene chloride to remove impurities and then 0.8% methanol/methylene chloride to give, after concentration of the product fractions in vacuum, 0.23 g of the (S)-enantiomer of the title compound as a white solid, m.p. 148-150° C.

Elemental Analysis for: $C_{25}H_{25}F_3N_2O_4$ Calc'd: C, 63.29; H, 5.31; N, 5.90 Found: C, 63.29; H, 5.26; N, 5.72

INTERMEDIATE 17

8-Benzyl-8-aza-bicyclo[3.2.1]octan-3-one

To a stirred solution of 29.2 g (209 mmole) tropinone in 300 mL of 1,2-dichloroethane was added 45.5 mL (419 mmole) 1-chloroethyl chloroformate, and the resulting solution was warmed to 80° C. The reaction was monitored by thin layer chromatography on a silica gel plate eluting with EtOAc/2M $NH_3$:MeOH (5:1). After stirring for 18 h, the solvent was evaporated, 300 mL MeOH was added, and the reaction was heated to reflux. After 45 min, the solvent was evaporated, then 300 mL THF, 38.83 g (227 mmol) benzyl bromide, and 33 mL (24.0 g, 237 mmol) triethylamine was added, and the resulting mixture was stirred at 23° C.

After 69 h, the mixture was transferred to a separatory funnel containing 200 mL sat. $NaHCO_3$ solution. The aqueous layer was extracted with EtOAc (2×300 mL), then the combined organics were washed with water (100 mL), brine (100 mL), dried over $MgSO_4$ filtered and evaporated to a brown oil. The crude material was purified by flash chromatography on $SiO_2$, using a gradient elution of $CH_2Cl_2$/EtOAc (40:1 to 20:1 to 8:1 to 4:1). The appropriate fractions were combined and evaporated to afford 19.91 g (92 mmol, a 44% yield) of the title compound as a yellow-orange oil. MS (ES) m/z. 216 $(MH)^+$.

INTERMEDIATE 18

8-Benzyl-3-naphthalen-2-yl-8-aza-bicyclo[3.2.1] octan-3-ol

To a −78° C. solution of 10.75 g (50.35 mmol) 2-bromonaphthalene in 200 mL THF was added 20.1 mL (50.25 mmol) of n-BuLi (2.5 M in hexanes) in drops over 5 min. After 35 min, a solution of 10.51 g (48.82 mmol) 8-benzyl-8-aza-bicyclo[3.2.1]octan-3-one in 25 mL THF was added via cannula, and then allowed to warm to room temperature. After 17 h, the mixture was transferred to a separatory funnel containing 200 mL brine. The aqueous layer was extracted with EtOAc (3×150 mL), then the combined organics were washed with water (100 mL), brine (100 mL), dried over $MgSO_4$, filtered and evaporated to an orange oil.

The crude material was purified by flash chromatography on $SiO_2$, using a gradient elution of $CH_2Cl_2$/EtOAc (40:1 to 20:1 to 8:1 to 4:1 to 2:1 to 1:1). The appropriate fractions were combined and evaporated to afford 7.07 g (20.6 mmol, a 42% yield) of the title compound as a yellow oil. MS (ES) m/z: 345 $(MH)^+$.

INTERMEDIATE 19

3-Naphthalen-2-yl-8-aza-bicyclo[3.2.1]octan-3-ol

To 3.80 g (11.1 mmol) 8-benzyl-3-naphthalen-2-yl-8-aza-bicyclo[3.2.1]octan-3-ol was added 1.20 g (19.0 mmol) of ammonium formate, 100 mL MeOH, and 2.46 g Pd/C (10 wt. %). The reaction mixture was heated to 50° C., and was monitored by TLC on a $SiO_2$ plate with $CHCl_3$:MeOH (10:1). After 21 h, the mixture was cooled to room temperature, filtered through a pad of celite and evaporated to afford 2.0 g (7.9 mmol, a 72% yield) of the title compound as an off-white solid. MS (ES) m/z: 344 $(MH)^+$.

EXAMPLE 3

8-{[2-Methyl-7,8-dihydro[1,4]dioxino[2,3-g][1,3] benzoxazol-8-yl]methyl}-3-(2-naphthyl)-8-azabicyclo[3.2.1]octan-3-ol (8R)-2-Methyl-7,8-dihydro[1,4]dioxino[2,3-g][1,3]benzoxazol-8-ylmethyl 4-methylbenzenesulfonate (0.40 g, 1.1 mmole) and 3-(2-naphthyl)-8-aza-bicyclo-[3.2.1]octan-3-ol (0.35 g, 1.4 mmole) were combined in 6.5 mL of DMSO. This solution was heated at 80° C. under nitrogen for 14 hours. After completion, the reaction was cooled to room temperature and diluted to 500 mL with ethyl acetate. The mixture was washed twice with 400 mL portions of saturated aqueous sodium bicarbonate, with 300 mL of water and twice with 400 mL of saturated brine, dried over sodium sulfate, filtered and concentrated in vacuum to give 0.43 g of a brown oil. The crude oil was column chromatographed on silica gel using first methylene chloride to remove impurities and then 0.8% methanol/methylene chloride to give, after concentration of the product fractions in vacuum, 0.12 g of the (S)-enantiomer of the title compound as an off-white solid, m.p. 192-195° C.

Elemental Analysis for: $C_{24}H_{26}N_2O_4 \cdot 0.20\ CH_2Cl_2$ Calc'd: C, 71.53; H. 6.05; N, 5.92 Found: C, 71.53; H, 6.19; N. 5.92

What is claimed is:

1. A method of treating a subject suffering from a condition selected from the group consisting of cognitive dysfunction, and schizophrenia which comprises providing to the subject suffering from said condition, a therapeutically effective amount of a compound of formula I

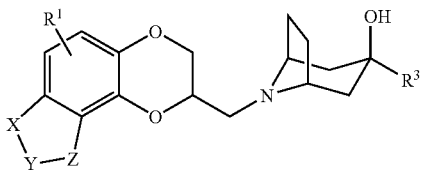

wherein
  $R^1$ is hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;
  X—Y-Z is N=C($R^2$)—O, N=C($R^2$)—NH or NH—C($R^2$)=CH;
  $R^2$ is hydrogen, halo, trifluoromethyl, amino, mono- or di-alkylamino in which each alkyl group has 1 to 6 carbon atoms, alkoxy of one to six carbon atoms or alkyl of one to six carbon atoms; and
  $R^3$ is phenyl, naphthyl, anthracyl, phenanthryl, pyridyl, pyrimidyl, triazinyl, thienyl, furyl, pyrrolyl, pyrazolyl, indolyl, imidazolyl, benzofuryl, benzothienyl, oxazolyl, or thiazolyl, each optionally substituted with from one to three substituents selected from the group consisting of hydroxy, halo, trifluoromethyl, cyano, amino, mono- or di-alkylamino in which each alkyl group has 1 to 6 carbon atoms, alkoxy of one to six carbon atoms and alkyl of one to six carbon atoms;
  or a pharmaceutically acceptable salt thereof.

2. The method of claim 1 wherein the subject is a human.

3. A method of treating a subject suffering from a condition selected from the group consisting of anxiety, aggression and stress which comprises providing to the subject suffering from said condition, a therapeutically effective amount of a compound of formula I

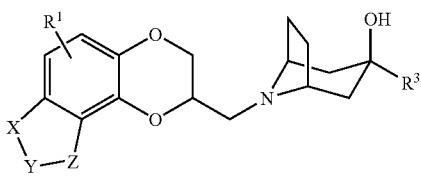

wherein
  $R^1$ is hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;
  X—Y-Z is N=C($R^2$)—O, N=C($R^2$)—NH or NH—C($R^2$)=CH;

$R^2$ is hydrogen, halo, trifluoromethyl, amino, mono- or di-alkylamino in which each alkyl group has 1 to 6 carbon atoms, alkoxy of one to six carbon atoms or alkyl of one to six carbon atoms; and
  $R^3$ is phenyl, naphthyl, anthracyl, phenanthryl, pyridyl, pyrimidyl, triazinyl, thienyl, furyl, pyrrolyl, pyrazolyl, indolyl, imidazolyl, benzofuryl, benzothienyl, oxazolyl, or thiazolyl, each optionally substituted with from one to three substituents selected from the group consisting of hydroxy, halo, trifluoromethyl, cyano, amino, mono- or di-alkylamino in which each alkyl group has 1 to 6 carbon atoms, alkoxy of one to six carbon atoms and alkyl of one to six carbon atoms;
  or a pharmaceutically acceptable salt thereof.

4. The method of claim 3 wherein the subject is a human.

5. A method of treating a subject suffering from a condition selected from the group consisting of eating disorders, disorders of thermoregulation, sleep dysfunction and sexual dysfunction which comprises providing to the subject suffering from said condition, a therapeutically effective amount of a compound of formula I

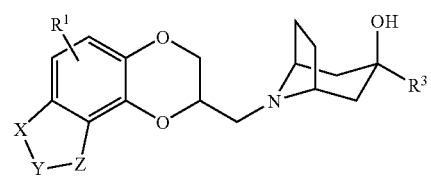

wherein
  $R^1$ is hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;
  X—Y-Z is N=C($R^2$)—O, N=C($R^2$)—NH or NH—C($R^2$)=CH;
  $R^2$ is hydrogen, halo, trifluoromethyl, amino, mono- or di-alkylamino in which each alkyl group has 1 to 6 carbon atoms, alkoxy of one to six carbon atoms or alkyl of one to six carbon atoms; and
  $R^3$ is phenyl, naphthyl, anthracyl, phenanthryl, pyridyl, pyrimidyl, triazinyl, thienyl, furyl, pyrrolyl, pyrazolyl, indolyl, imidazolyl, benzofuryl, benzothienyl, oxazolyl, or thiazolyl, each optionally substituted with from one to three substituents selected from the group consisting of hydroxy, halo, trifluoromethyl, cyano, amino, mono- or di-alkylamino in which each alkyl group has 1 to 6 carbon atoms, alkoxy of one to six carbon atoms and alkyl of one to six carbon atoms;
  or a pharmaceutically acceptable salt thereof.

6. The method of claim 5 wherein the subject is a human.

7. A method of treating a subject suffering depression comprising providing to the subject suffering from said condition, an antidepressant amount of a serotonin selective reuptake inhibitor and an amount of a compound of formula I

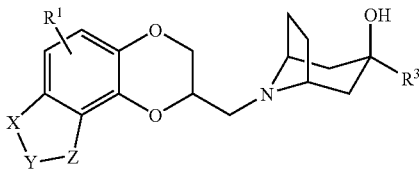

wherein
R¹ is hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

X—Y-Z is N=C(R²)—O, N=C(R²)—NH or NH—C(R²)=CH;

R² is hydrogen, halo, trifluoromethyl, amino, mono- or di-alkylamino in which each alkyl group has 1 to 6 carbon atoms, alkoxy of one to six carbon atoms or alkyl of one to six carbon atoms; and R³ is phenyl, naphthyl, anthracyl, phenanthryl, pyridyl, pyrimidyl, triazinyl, thienyl, furyl, pyrrolyl, pyrazolyl, indolyl, imidazolyl, benzofuryl, benzothienyl, oxazolyl, or thiazolyl, each optionally substituted with from one to three substituents selected from the group consisting of hydroxy, halo, trifluoromethyl, cyano, amino, mono- or di-alkylamino in which each alkyl group has 1 to 6 carbon atoms, alkoxy of one to six carbon atoms and alkyl of one to six carbon atoms;

or a pharmaceutically acceptable salt thereof; said amount being effective to increase the onset of antidepressant efficacy.

8. The method of claim 7 wherein the subject is a human.

9. The method of claim 7 wherein the serotonin selective reuptake inhibitor is fluoxetine, venlafaxine, duloxetine, sertraline, paroxetine, fluvoxamine, nefazodone, or mirtazapine.

10. A method of claim 7 wherein X—Y-Z is N=C(R²)—O.

11. A method of claim 7 wherein R¹ is hydrogen, halo, trifluoromethyl, alkyl of 1 to 6 carbon atoms, alkoxy of 1 to 6 carbon atoms, amino, mono- or di-alkylamino in which each alkyl group has 1 to 6 carbon atoms.

12. A method of claim 7 wherein R¹ is hydrogen, trifluoromethyl, alkyl of one to six carbon atoms or alkoxy of one to six carbon atoms.

13. A method of claim 7 wherein R² is hydrogen, trifluoromethyl, amino, mono- or dialkylamino in which each alkyl group has one to six carbon atoms, or alkyl of 1 to 6 carbon atoms.

14. A method of claim 7 wherein R² is hydrogen, trifluoromethyl, or alkyl of one to six carbon atoms.

15. A method of claim 7 wherein R³ is phenyl, naphthyl, pyridyl, pyrimidyl, thienyl, furyl, pyrrolyl, pyrazolyl, indolyl, imidazolyl, benzofuryl, or benzothienyl, each optionally substituted with from one to three substituents selected from the group consisting of hydroxy, halo, trifluoromethyl, cyano, amino, mono- or di-alkylamino in which each alkyl group has 1 to 6 carbon atoms, alkoxy of one to six carbon atoms and alkyl of one to six carbon atoms.

16. A method of claim 7 wherein R³ is phenyl, naphthyl, pyridyl, pyrrolyl, indolyl, or benzothienyl, each optionally substituted with from one to three substituents selected from the group consisting of halo, trifluoromethyl, cyano, alkoxy of one to six carbon atoms and alkyl of one to six carbon atoms.

17. A method of claim 7 wherein R³ is phenyl or naphthyl, each optionally substituted with from one to three substituents selected from the group consisting of halo, trifluoromethyl, cyano, alkoxy of one to six carbon atoms and alkyl of one to six carbon atoms.

18. A method of claim 7 in which R¹ is hydrogen, halo, trifluoromethyl, alkyl of one to six carbon atoms, alkoxy of one to six carbon atoms, amino, mono- or di-alkylamino in which each alkyl group has one to six carbon atoms; R² is hydrogen, trifluoromethyl, amino, mono- or di-alkylamino in which each alkyl group has one to six carbon atoms, or alkyl of one to six carbon atom; and R³ is phenyl, naphthyl, pyridyl, pyrimidyl, thienyl, furyl, pyrrolyl, pyrazolyl, indolyl, imidazolyl, benzofuryl, or benzothienyl, each optionally substituted with from one to three substituents selected from the group consisting of hydroxy, halo, trifluoromethyl, cyano, amino, mono- or di-alkylamino in which each alkyl group has 1 to 6 carbon atoms, alkoxy of one to six carbon atoms and alkyl of one to six carbon atoms; or a pharmaceutically acceptable salt thereof.

19. A method of claim 7 in which R¹ is hydrogen, halo, trifluoromethyl, alkyl of one to six carbon atoms or alkoxy of one to six carbon atoms; R² is hydrogen, trifluoromethyl or alkyl of one to six carbon atom; and R³ is phenyl, naphthyl, pyridyl, pyrrolyl, indolyl, or benzothienyl, each optionally substituted with from one to three substituents selected from the group consisting of halo, trifluoromethyl, cyano, alkoxy of one to six carbon atoms and alkyl of one to six carbon atoms; or a pharmaceutically acceptable salt thereof.

20. A method of claim 7 wherein the compound of formula I is 8-{[2-methyl-7,8-dihydro[1,4]-dioxino[2,3-g][1,3]benzoxazol-8-yl]methyl}-3-phenyl-8-azabicyclo[3.2.1]octan-3-ol; 8-{[2-methyl-7,8-dihydro[1,4]dioxino[2,3-g][1,3]benzoxazol-8-yl]methyl}-3-[3-(trifluoromethyl)-phenyl]-8-azabicyclo[3.2.1]octan-3-ol; 8-{[2-methyl-7,8-dihydro[1,4]-dioxino[2,3-g][1,3]benzoxazol-8-yl]methyl}-3-(2-naphthyl)-8-azabicyclo[3.2.1]-octan-3-ol; or a pharmaceutically acceptable salt thereof.

* * * * *